US011839717B2

United States Patent
Heinonen et al.

(10) Patent No.: US 11,839,717 B2
(45) Date of Patent: Dec. 12, 2023

(54) MINUTE VOLUME AND CARBON DIOXIDE CLEARANCE AS SURROGATES FOR $ETCO_2$ IN AUTOMATIC VENTILATION

(71) Applicant: GENERAL ELECTRIC COMPANY, Schenectady, NY (US)

(72) Inventors: Erkki Paavo Heinonen, Helsinki (FI); Tom Jakob Haggblom, Vantaa (FI); Pietari Aleksis Kokko, Espoo (FI)

(73) Assignee: General Electric Company, Schenectady, NY (US)

( * ) Notice: Subject to any disclaimer, the term of this patent is extended or adjusted under 35 U.S.C. 154(b) by 1208 days.

(21) Appl. No.: 14/970,084

(22) Filed: Dec. 15, 2015

(65) Prior Publication Data

US 2016/0184546 A1 Jun. 30, 2016

Related U.S. Application Data

(63) Continuation-in-part of application No. 14/586,383, filed on Dec. 30, 2014, now Pat. No. 9,775,959.

(51) Int. Cl.
*A61M 16/00* (2006.01)
*A61M 16/10* (2006.01)
(Continued)

(52) U.S. Cl.
CPC ......... *A61M 16/0051* (2013.01); *A61M 16/04* (2013.01); *A61M 16/06* (2013.01);
(Continued)

(58) Field of Classification Search
CPC .. A61M 16/00; A61M 16/022; A61M 16/024; A61M 16/04; A61M 16/06;
(Continued)

(56) References Cited

U.S. PATENT DOCUMENTS 5,720,277 A * 2/1998 Olsson .................. A61M 16/00
128/203.12
2004/0049113 A1 * 3/2004 Orr .................... A61M 16/0833
600/481

(Continued)

OTHER PUBLICATIONS

Fernando, T. et al; Automatic Control of Arterial Carbon Dioxide Tension in Mechanically Ventilated Patients; IEEE Transactions on Information Technology in Biomedicine; vol. 6, No. (4); 269-276; Published Dec. 2002.

*Primary Examiner* — Rachel T Sippel
*Assistant Examiner* — Jacqueline M Pinderski
(74) *Attorney, Agent, or Firm* — ANDRUS INTELLECTUAL PROPERTY LAW, LLP

(57) ABSTRACT

A method for automatically controlling ventilation of a patient includes receiving a target expiratory $CO_2$ concentration, measuring an actual expiratory $CO_2$, and comparing the actual expiratory $CO_2$ concentration to the target expiratory $CO_2$. A ventilation rate for the patient is then calculated based on the comparison of the actual expiratory $CO_2$ concentration and the target expiratory $CO_2$ in order to maintain the actual expiratory $CO_2$ within a predetermined range of the target expiratory $CO_2$. The patient is then automatically ventilated based on the calculated ventilation rate.

26 Claims, 8 Drawing Sheets

(51) Int. Cl.
*A61M 16/06* (2006.01)
*A61M 16/04* (2006.01)

(52) U.S. Cl.
CPC ............ *A61M 2016/103* (2013.01); *A61M 2205/3569* (2013.01); *A61M 2205/3592* (2013.01); *A61M 2205/502* (2013.01); *A61M 2205/505* (2013.01); *A61M 2205/52* (2013.01); *A61M 2230/42* (2013.01); *A61M 2230/432* (2013.01)

(58) Field of Classification Search
CPC .... A61M 16/0051; A61M 16/10–1005; A61M 2016/0413; A61M 2016/102; A61M 2016/103; A61M 2205/502; A61M 2205/52; A61M 2230/40; A61M 2230/42; A61M 2230/43; A61M 2230/432
See application file for complete search history.

(56) References Cited

U.S. PATENT DOCUMENTS

| | | | |
|---|---|---|---|
| 2008/0236581 A1 | 10/2008 | Rantala et al. | |
| 2009/0120435 A1* | 5/2009 | Slessarev | A61M 16/08 128/203.14 |
| 2011/0041850 A1* | 2/2011 | Vandine | A61M 16/0051 128/204.23 |
| 2011/0082380 A1* | 4/2011 | Breen | A61M 16/12 600/532 |
| 2013/0032147 A1* | 2/2013 | Robinson | A61M 16/0051 128/204.18 |
| 2015/0034082 A1* | 2/2015 | Kimm | A61M 16/0051 128/202.16 |
| 2015/0114394 A1* | 4/2015 | Klein | A61M 16/026 128/203.25 |

* cited by examiner

MINUTE VOLUME AND CARBON DIOXIDE CLEARANCE AS SURROGATES FOR ETCO₂ IN AUTOMATIC VENTILATION

BACKGROUND

Current ventilation systems require control by a clinician, who inputs control values for the ventilator, including ventilation rate and gas values. For example, during surgery and in an intensive care unit a patient is ventilated mechanically by a mechanical ventilator that is controlled by a clinician. In such applications, end tidal $CO_2$ ($EtCO_2$) is often measured to evaluate ventilation adequacy and to supervise patient status. Changes in $EtCO_2$ can be an indication of metabolic and/or hemodynamic changes in a patient, and thus $EtCO_2$ is a valuable monitoring parameter to clinicians.

Currently available systems that require clinician control are prone to user error. Thus, it is desirable to create an automated ventilation system that eliminates the requirement of clinician control. If administered properly, automatic ventilation control can eliminate user error and provide a safer ventilation control to a patient. However, choosing the right control variables and effectuating the automatic control algorithms is challenging because the human respiratory system is a complicated system with many variables that must be accounted for.

SUMMARY

In one embodiment, a method for automatically controlling ventilation of a patient includes receiving a target expiratory $CO_2$ concentration, measuring an actual expiratory $CO_2$, and comparing the actual expiratory $CO_2$ concentration to the target expiratory $CO_2$. A ventilation rate for the patient is then calculated based on the comparison of the actual expiratory $CO_2$ concentration and the target expiratory $CO_2$ in order to maintain the actual expiratory $CO_2$ within a predetermined range of the target expiratory $CO_2$. The patient is then automatically ventilated based on the calculated ventilation rate.

Another embodiment of a method for automatically controlling ventilation of a patient includes receiving a target $EtCO_2$ for the patient, receiving an alveolar minute volume value for the patient, measuring an expiratory $CO_2$ in a gas expired from the patient, and then calculating an actual $EtCO_2$. The actual $EtCO_2$ is compared to the target $EtCO_2$. If the actual $EtCO_2$ is not within a predetermined range of the target $EtCO_2$, then the alveolar minute volume value is adjusted and the patient is automatically ventilated using the adjusted alveolar minute volume value. A change in patient status is then indicated.

An embodiment for a system for automatically ventilating a patient includes a ventilator, a gas analyzer, a controller, and a display. The controller automatically controls the ventilator to ventilate the patient. The controller receives a target $EtCO_2$ for the patient and an initial alveolar minute volume value for the patient. The controller also receives the actual $EtCO_2$ from a gas analyzer. The controller then compares the actual $EtCO_2$ to the target $EtCO_2$. If the actual $EtCO_2$ is not within a predetermined range of the target $EtCO_2$, then the controller calculates an adjusted alveolar minute volume value and automatically ventilating the patient based on the adjusted alveolar minute volume value.

BRIEF DESCRIPTION OF THE DRAWINGS

The drawings illustrate the best mode presently contemplated of carrying out the disclosure. In the drawings.

DETAILED DESCRIPTION OF THE DRAWINGS

Figure 1:
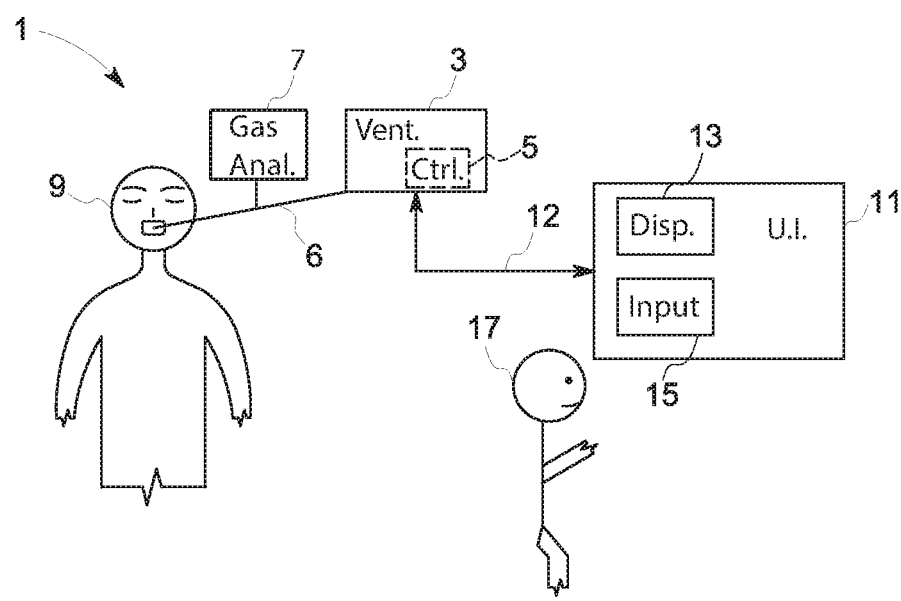
FIG. 1 depicts one embodiment of an automatic ventilation system.

The present inventors have recognized that in automatic ventilation the expiratory $CO_2$ concentration, such as $EtCO_2$, can be used as a control parameter. This means that the controller may adjust ventilation automatically to maintain $EtCO_2$ at a given target value. However, the inventors have recognized that automatically maintaining $EtCO_2$ at a given target value via an automated ventilation system could be problematic because the system controller may not be capable of determining the cause of changes in $EtCO_2$, as it cannot differentiate between all of the potential reasons that may lead to $EtCO_2$ changes. Furthermore, since the controller would keep $EtCO_2$ at a constant value by adjusting other ventilation parameters, a clinician would not see changes in a patient's $EtCO_2$ value, and thus valuable information about a patient's physiological status may be lost. Adequate information must be provided to a clinician indicating a patient's metabolic and hemodynamic states. The present inventors have realized that ventilation rate can be used alongside target expiratory $CO_2$ concentration to indicate changes in a patient hemodynamic and metabolic status. In the present invention, expiratory $CO_2$ concentration is kept constant with automatic control. In a preferred embodiment, $EtCO_2$ is used as the parameter indicating expiratory $CO_2$ concentration.

Automatically ventilating a patient by using $EtCO_2$ as a control parameter differs from currently available or practiced ventilation techniques and systems. Traditionally, clinicians control ventilation by setting a ventilation rate on the ventilator which is kept constant throughout the ventilation process unless the clinician manually adjusts the ventilation rate. For example, minute volume (MV), including minute alveolar volume ($MV_{alv}$), is kept constant at a value set by a clinician. The clinician may change the input value, for example, upon seeing a need to compensate for a change in a patient's $EtCO_2$ value, which is allowed to fluctuate and is monitored as an output value indicating patient status. For example, in currently available ventilation control methods $EtCO_2$ may vary as much as +/−10% from an optimum or anticipated value before a clinician manually adjusts ventilation parameters to compensate for an $EtCO_2$ change. Thus, in current ventilation systems, ventilation rate is set by a user and changes in expiratory $CO_2$ concentration, such as the $EtCO_2$ value, indicate a change in the hemodynamic and/or metabolic status of the patient.

The present inventors recognized that the challenges posed by deficiency of information when expiratory $CO_2$ concentration is kept constant can be overcome by reporting changes in ventilation rate, such as changes in $MV_{alv}$, to indicate a change in patient hemodynamic and/or metabolic status. By the present invention, patient hemodynamic and metabolic monitoring during ventilation where ventilation rate is automatically adjusted to minimize variation in measured patient expiratory $CO_2$ concentration is conducted by adjusting the ventilation rate to maintain an approximately constant expiratory $CO_2$ concentration and reporting the change in the ventilation rate to indicate a change in the patient hemodynamic and/or metabolic status. For example, in automatic ventilation control according to the present invention, a target $EtCO_2$ value may be set by a clinician and changes in $MV_{alv}$ may be reported to indicate a change in patient hemodynamic and/or metabolic status. In one embodiment of such a system, the target $EtCO_2$ value automatically maintained by a ventilation control system is shown together in the same view as the calculated $MV_{alv}$ value so that a clinician can monitor a patient's status. Because $MV_{alv}$ has always been held constant in current and prior ventilation systems, it is not obvious that $MV_{alv}$ can be presented as a patient parameter.

The present inventors also recognized that the challenges posed by deficiency of information when expiratory $CO_2$ concentration is kept constant can be overcome by reporting changes in carbon dioxide clearance ($VCO_2$), to indicate a change in patient hemodynamic and/or metabolic status. For example, in automatic ventilation control according to the present invention, a target $EtCO_2$ value may be set by a clinician and changes in $VCO_2$ may be reported to indicate a change in patient hemodynamic and/or metabolic status. In one embodiment of such a system, the target $EtCO_2$ value automatically maintained by a ventilation control system is shown together in the same view as the $VCO_2$ value so that a clinician can monitor a patient's status.

For the purposes herein, it should be appreciated that carbon dioxide clearance may be referred to as carbon dioxide elimination or carbon dioxide production, and the abbreviation $VCO_2$ should refer to all of the aforementioned terms. It should further be appreciated that carbon dioxide clearance may be measured through integration of the product of breathing gas flow and its $CO_2$ concentration, or alternatively, approximated using the measured or target $EtCO_2$ multiplied with the alveolar ventilation ($MV_{alv}$) as $VCO_2 = EtCO_2 \times MV_{alv}$.

As shown in FIG. 1, an automatic ventilation system 1 comprises a ventilator 3 connected to a patient 9 through a breathing circuit 6. The breathing circuit may include an endotracheal tube or a mask to connect the breathing circuit 6 to the patient 9. A gas analyzer 7 is connected to the breathing circuit 6 such that it can analyze gas expired by the patient 9. The gas analyzer 7 may be, for example, a time capnogram. Time-based capnography, such as $EtCO_2$ monitoring, is widely used in ventilation applications, including anesthesia and ICU applications. Time capnographs make use of main-stream sensors or side stream sensors. Volumetric capnography, which provides direct measurement of $VCO_2$, requires specialized equipment that is not widely available. Accordingly, one benefit of the presently disclosed method and system is that patient $CO_2$ monitoring is provided using the widely available time-based capnography equipment, as $MV_{alv}$ estimation does not require any extra hardware than that available on currently available ventilation systems. Volumetric capnography, on the other hand, requires a separate device that is often not available in many ventilation applications, such as in the operating room or in the ICU. Accordingly, the gas analyzer 7 indirectly reflects the production of $CO_2$ by the patient's tissues and the patient's circulatory transport of $CO_2$ to the lungs.

The ventilator 3 is controlled by controller 5, which may be any type of controller capable of automatically controlling the ventilator 3. For example, the controller may be control software integrated into the control module in an anesthesia machine. Alternatively, the controller may be control software stored and executed on a separate computing device, such as a laptop, used in conjunction with an anesthesia machine or other ventilator. It is to be recognized that the controller 5 may be any combination of software and hardware implemented to perform the methods disclosed here in, and may include one or more processors that are communicatively connected so as to cooperate in providing a control function. The controller 5 may further comprise a microprocessor and other circuitry that retrieves and executes software from a storage system. Examples of processors include general purpose central processing units, application specific processors, and logic devices, as well as any other type of processing device, combinations of processing devices, or variations thereof. The storage system can comprise any storage media readable by processing system, and capable of storing software for the execution of control algorithms. The storage system can include volatile and non-volatile, removable and non-removable media implemented in any method or technology for storage of information, such as computer readable instructions, data structures, program modules, or other data.

A user interface 11 is provided to allow an operator 17 to interact with and/or monitor the controller 5 and the ventilator 3. The user interface is connected to the ventilator 3 and/or the controller 5 via connection 12. Connection 12 may be any wired or wireless connection between the ventilator 3 and the user interface 11. For example, the connection 12 may utilize Wi-Fi, Bluetooth, or wireless medical telemetry service (WMTS) technology, or any other wireless technology available. In other embodiments, the connection 12 may be a physical wired data connection. The user interface 11 may have a display 13 and an input device 15. The user interface 11, display 13, and input device 15 may be any device or devices that allow an operator 17 to interface with the ventilator 1 and controller 5 to oversee and control the automatic ventilation of a patient. The user interface 11 may be integrated into an anesthesia cart or provided separate from an anesthesia cart. For example, the user interface 11 may be integrated into an anesthesia cart as a touch screen that acts as a display 13 to display monitoring data from the patient 9 and output data from the automatic ventilation system 1, and also to allow an operator 17 to input control commands to the system. In other embodiments, the user interface 11 may include a mouse, a keyboard, a voice input device, any touch input device for receiving a gesture from a user, a motion input device for detecting non-touch gestures and other motions by a user, and other comparable input devices and associated processing elements capable of receiving user input from a user. Output devices such as a video display or graphical display can display an interface further associated with embodiments of the system and method as disclosed herein. Speakers, printers, haptic devices and other types of output devices may also be included in the user interface 11.

Expired $CO_2$ concentration can be related to the expired volume over time to yield $CO_2$ elimination ($VCO_2$) rate, which is an important measure of patient metabolism and hemodynamic status. For example, sudden changes in $CO_2$ elimination during lung or heart surgery often imply important changes in cardiorespiratory function. For example, changes in a patient's $EtCO_2$ value or $MV_{alv}$ value would be used by clinicians to provide indication of a change in cardiorespiratory function. Similarly, when one of these parameters ($EtCO_2$ or $MV_{alv}$) is maintained constant, changes in the other parameter may be used to detect lung conditions such as a pulmonary embolism, hemodynamic conditions such as a drop in cardiac output, or metabolic conditions such as metabolic hyperactivity. The automatic ventilation system 1 includes controller 5 configured to keep the patient's expiratory $CO_2$ concentration at a target value by controlling the ventilation rate. In the present disclosure, the $CO_2$ concentration measurement is exemplified as $EtCO_2$ and ventilation rate is exemplified as alveolar minute volume ($MV_{alv}$). However, it is contemplated that other parameters may be used to gauge patient ventilation rate, including minute volume. It is further contemplated that other parameters indicating expiratory $CO_2$ concentrations may be used other than $EtCO_2$.

Both $MV_{alv}$ and $EtCO_2$ measurements track carbon dioxide production ($VCO_2$). The $MV_{alv}$ value is an effective patient monitoring value because it reflects changes in patient status very well. $MV_{alv}$ is the net effect of all of the ventilation rate settings and variables, including tidal volume, respiration rate, and dead space. Thus, $MV_{alv}$ is a sensitive variable. Further, the inventors have recognized that $MV_{alv}$ has more fluctuation and sensitivity than $EtCO_2$ for the same patient situation, and thus may provide more immediate detection of changes in patient metabolic or hemodynamic status. $MV_{alv}$ has high sensitivity because it is primarily a controlled variable.

$MV_{alv}$ may be defined as $MV_{alv}=MV-DS \times RR$ wherein MV is minute volume, DS is estimated dead space for the patient, and RR is respiration rate. $VCO_2$ can be depicted as a product of both $MV_{alv}$ and $EtCO_2$ where $VCO_2=EtCO_2 \times MV_{alv}$. Thus, carbon dioxide production trends can be reported and visualized using $MV_{alv}$ values in place of $EtCO_2$ values.

Figure 2:
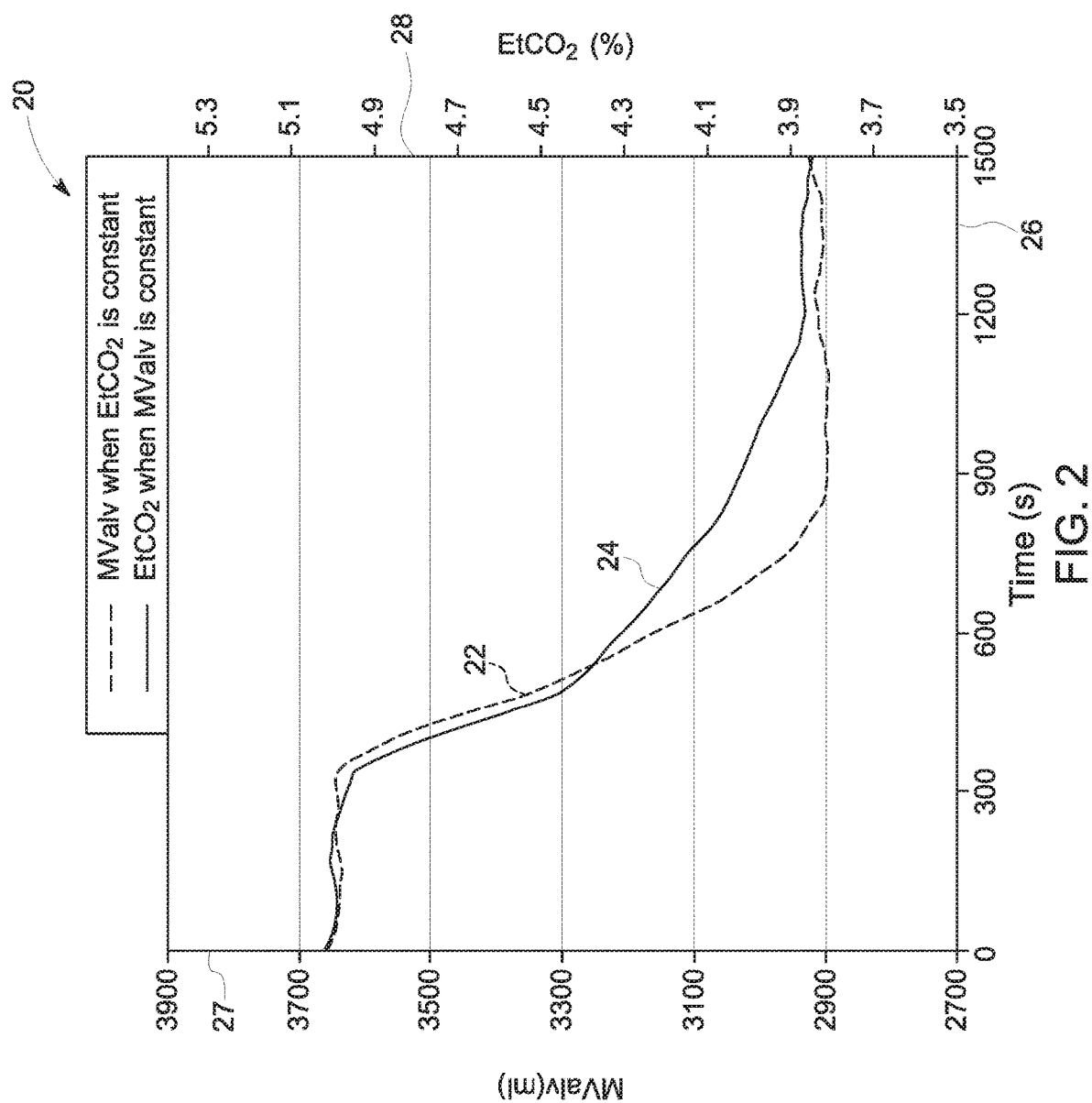
FIG. 2 depicts a graph comparing measured $EtCO_2$ changes where $MV_{alv}$ is held constant to measured changes in the $MV_{alv}$ value when $EtCO_2$ is automatically maintained at a constant level according to the methods and systems disclosed herein.

The technical feasibility of using $MV_{alv}$ as a patient parameter and as a variable for controlling $EtCO_2$, and thus $VCO_2$, was tested and the results of the feasibility testing are exemplified in FIG. 2. FIG. 2 depicts a graph 20 comparing measured $EtCO_2$ changes where $MV_{alv}$ is held constant (line 24), as is done in current ventilation systems, and measurement of changes in the $MV_{alv}$ value when $EtCO_2$ is automatically maintained at a constant level (line 22) according to the methods and systems disclosed herein. In FIG. 2, the x axis 26 depicts time, while the y axis 27 and 28 depicts either the $MV_{alv}$ value 27 corresponding to line 22 or the $EtCO_2$ value 28 corresponding to line 24. Tests were performed with a physical patient simulator which was ventilated with an anesthesia machine and automatic ventilation control. The patient simulator $CO_2$ production was changed to simulate a change in patient metabolism. FIG. 2 depicts the results, which show that a change in the $MV_{alv}$ value effectuated by the automatic controller was reflected in the $EtCO_2$ value (line 22). More specifically, a 20% change in $MV_{alv}$ value (line 22) corresponded to approximately a 20% change in the $EtCO_2$ value (line 24).

Figure 3:
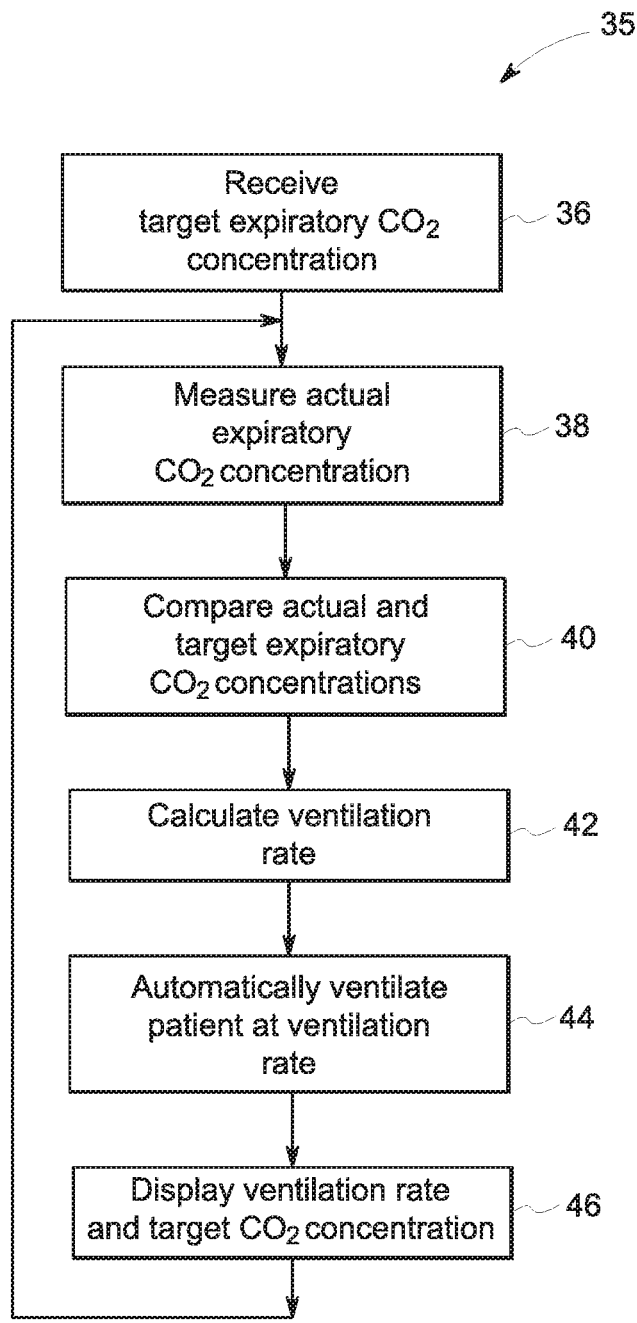
FIG. 3 depicts one embodiment of a method of automatically ventilating a patient.

FIG. 3 depicts one embodiment of a method of automatic ventilation control 35. A target expiratory $CO_2$ concentration is received at step 36. For example, the target expiratory $CO_2$ concentration value may be set by an operator, such as a clinician. At step 38, $CO_2$ levels are measured in a gas expired by a patient to determine an actual expiratory $CO_2$ level. At step 40, the actual expiratory $CO_2$ concentration is compared to the target $CO_2$ concentration. Then, a ventilation rate may calculated at step 42 based on the comparison between the actual expiratory $CO_2$ concentration and the target expiratory $CO_2$ concentration. For example, if the actual expiratory $CO_2$ concentration equals the target expiratory $CO_2$ concentration, then the ventilation rate may be maintained at a current ventilation rate. Alternatively, the ventilation rate may be increased if the actual expiratory $CO_2$ concentration is higher than the target expiratory $CO_2$ concentration. At step 44, the system automatically ventilates the patient at the ventilation rate determined or calculated at step 42. Then, the ventilation rate calculated at step 42 is displayed on a display at step 46, along with the target expiratory $CO_2$ concentration.

In other embodiments, minute volume or tidal volume may be adjusted in volume controlled ventilation in response to a determination that the actual expiratory $CO_2$ concentration is not equal to the target expiratory $CO_2$ concentration. In a pressure controlled ventilation system, minute volume or inspired pressure may be adjusted instead of or in addition to ventilation rate.

Figure 6:
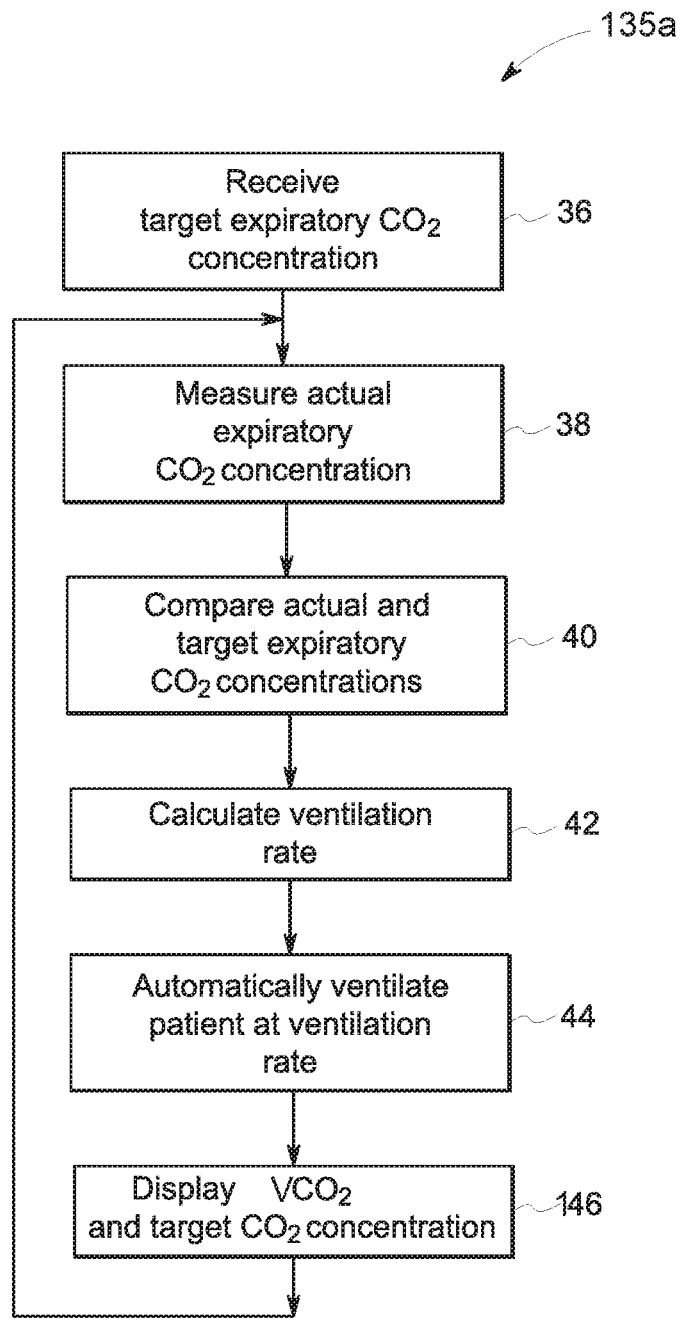
FIG. 6 depicts an embodiment of a method of automatically ventilating a patient.

In another embodiment, such as that depicted in FIG. 6, method 135a may include the steps 36, 38, 40, 42, and 44 as described with respect to FIG. 3. Then, at step 146, the carbon dioxide clearance ($VCO_2$) is displayed along with the target expiratory $CO_2$ concentration on a display.

Figure 4:
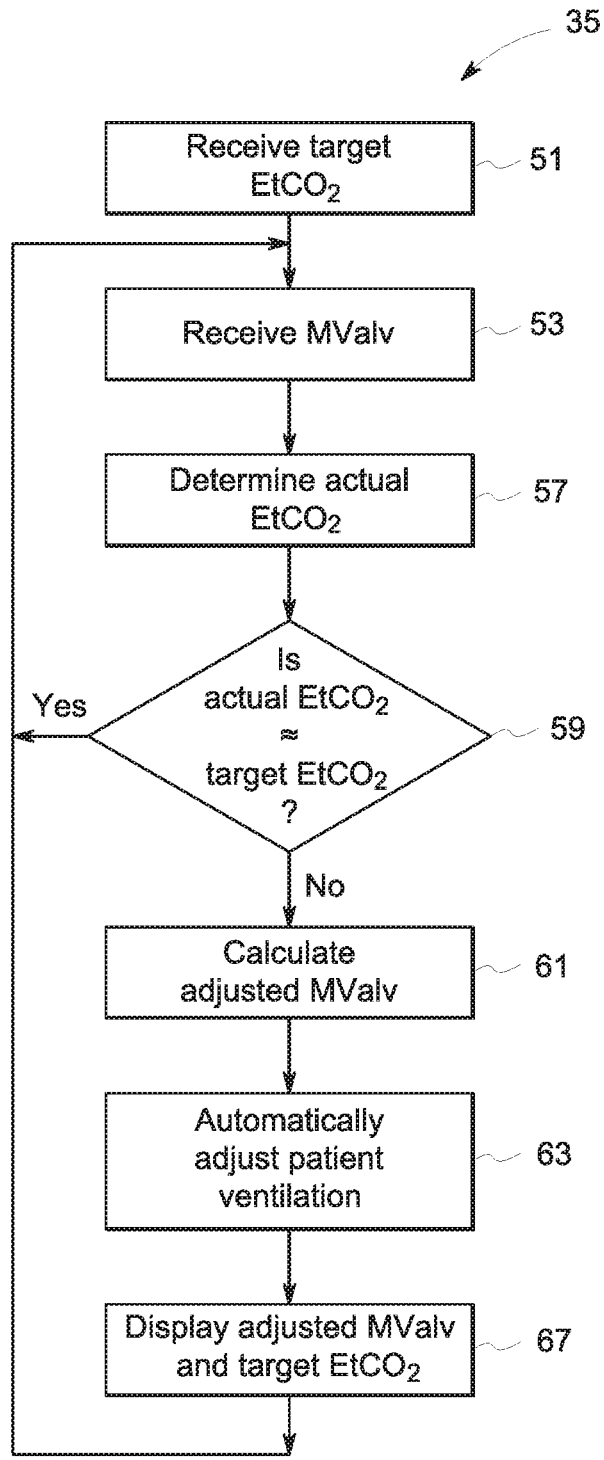
FIG. 4 depicts another embodiment of a method of automatically ventilating a patient.

FIG. 4 demonstrates another embodiment of a method for automatically ventilating a patient 35. At step 51, a target $EtCO_2$ value is received. For example, the target $EtCO_2$ value may be set by an operator. At step 53, an $MV_{alv}$ value is received, which is the alveolar minute volume currently delivered to the patient. An actual $EtCO_2$ is determined at step 57 for the patient, such as based on a measurement of $CO_2$ in gas expired by the patient. For example, the gas analyzer measures expiratory $CO_2$ in a gas expired from the patient and then calculates an actual $EtCO_2$ based on the expiratory $CO_2$ measurement. At step 59, the actual $EtCO_2$ is compared to the target $EtCO_2$ to determine whether the actual $EtCO_2$ is approximately equal to the target $EtCO_2$. For example, the system may determine whether the actual $EtCO_2$ is within a 0.01% predetermined range of the target $EtCO_2$. In another embodiment, the system may determine whether the actual $EtCO_2$ is within a 0.5% predetermined range of the target $EtCO_2$. Preferably, the system determines that the actual $EtCO_2$ is not approximately equal to the target $EtCO_2$ if the difference between the actual and target $EtCO_2$ values is greater than 0.5%. However, it is contemplated that the system may be more sensitive and require the actual $EtCO_2$ to be closer than 0.5% to the target $EtCO_2$ in order to be considered approximately equal. In another embodiment, the system may require the actual $EtCO_2$ to be precisely equal to the target $EtCO_2$ within the measurement sensitivity of the system. If the actual $EtCO_2$ is equal to or approximately equal to the target $EtCO_2$ at step 59, then no change is made to the patient ventilation at that time and the monitoring and control method restarts at step 53 where the current $MV_{alv}$ value is received for the current patient ventilation.

If the actual $EtCO_2$ is not equal to or approximately equal to the target $EtCO_2$, then the system continues to step 61 where an adjusted $MV_{alv}$ value is calculated. The adjusted $MV_{alv}$ value may be calculated based on the difference between the actual $EtCO_2$ value and the target $EtCO_2$ value. The $MV_{alv}$ value is adjusted with the goal of bringing the actual $EtCO_2$ value within the predetermined range of the target $EtCO_2$ value. Then, at step 63, the patient ventilation is automatically adjusted to comport with the adjusted $MV_{alv}$ value calculated at step 61. For example, the $MV_{alv}$ value is translated into ventilation parameters for the patient, such as respiration rate or respiration volume, and then the patient ventilation is changed to reflect the adjusted ventilation parameters. Once the ventilation parameters are automatically adjusted at step 63, the adjusted $MV_{alv}$ values are displayed at step 67, such as by display 12, and the control method returns to step 53 where the adjusted $MV_{alv}$ value is received as the new current $MV_{alv}$ value for the patient respiration.

Figure 5:
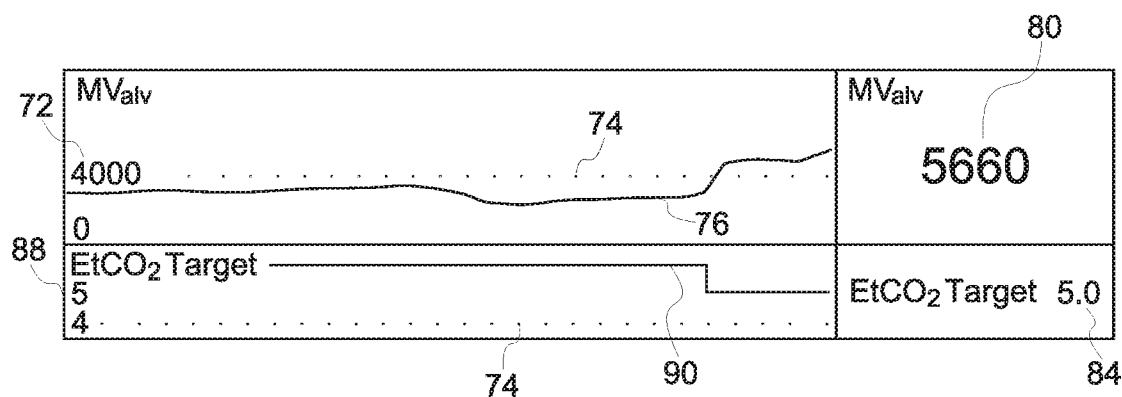
FIG. 5 depicts an exemplary output display presenting an $MV_{alv}$ value and a target $EtCO_2$ value for a patient over time.

At step 67, the adjusted $MV_{alv}$ value and target $EtCO_2$ may be displayed to an operator, such as a clinician. For example, the display, such as display 12, may provide the $MV_{alv}$ value over time, and the display may be updated at step 67 to reflect the adjusted $MV_{alv}$ value. FIG. 5 depicts one exemplary display presenting an $MV_{alv}$ value and a target $EtCO_2$ value for a patient over time. The upper portion of the exemplary display presents an $MV_{alv}$ trend line 76 showing the $MV_{alv}$ value over a time scale 74. The $MV_{alv}$ magnitude scale 72 is shown on the left hand side. The current $MV_{alv}$ value 80 is also shown. The lower portion of the exemplary display presents trend line 90 showing a target $EtCO_2$ over time (scale 74). The $EtCO_2$ magnitude scale 88 is shown in the lower left corner. The current $EtCO_2$ target value setting 84 is also shown below the current $MV_{alv}$ value 80. In other embodiments, $MV_{alv}$ may be replaced with minute volume or any other ventilation rate parameter. In such embodiments, the display may provide the ventilation rate parameter over time and the current value for the ventilation rate parameter in the same manner as shown and described in the exemplary embodiment of FIG. 5.

In one embodiment, the control system may alert a clinician if the $MV_{alv}$ value changes by more than a predetermined amount. The predetermined amount for the threshold $MV_{alv}$ change may be adjustable, for example by an operator 17 setting the threshold value through input device 15 (FIG. 1). For example, the system may provide an alert or an alarm if the $MV_{alv}$ value changes by more than 20% from a stable value.

Figure 7:
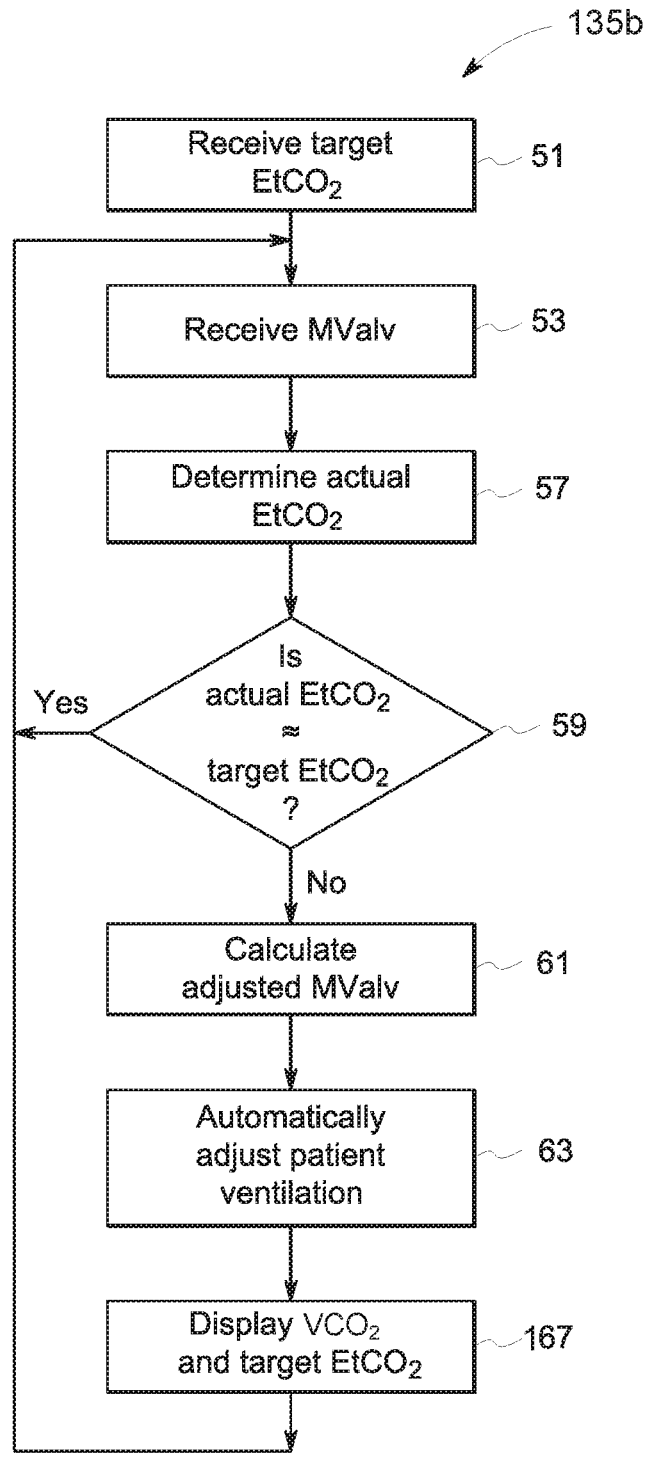
FIG. 7 depicts yet another embodiment of a method of automatically ventilating a patient.
Figure 8:
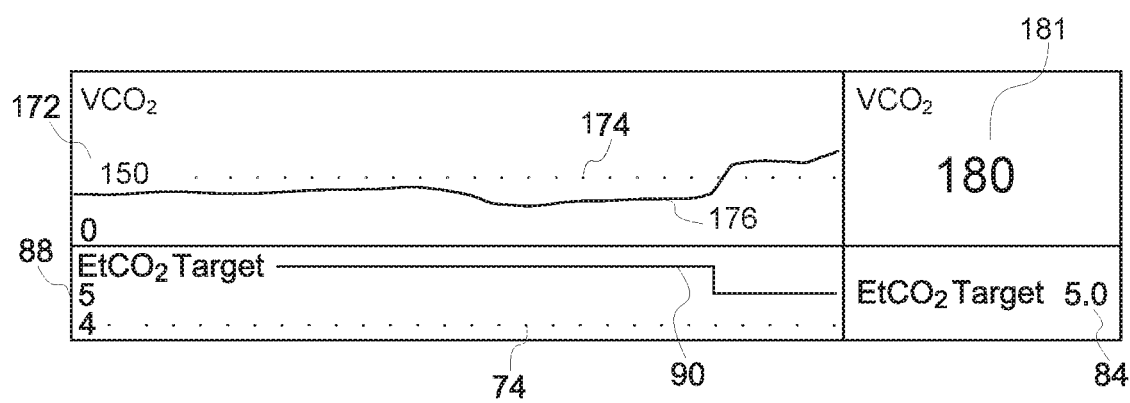
FIG. 8 depicts an exemplary output display presenting a $VCO_2$ value and a target $EtCO_2$ value for a patient over time.

FIG. 7 demonstrates another embodiment of a method for automatically ventilating a patient 35. The method 135*b* is similar to the method 35 of FIG. 4, with the exception of step 167. At step 167, the $VCO_2$ value and target $EtCO_2$ may be displayed to an operator, such as a clinician. For example, the display, such as display 12, may provide the $VCO_2$ value over time, and the display may be updated at step 167 to reflect the $VCO_2$ value. FIG. 8 depicts one exemplary display presenting a $VCO_2$ value and a target $EtCO_2$ value for a patient over time. The upper portion of the exemplary display presents a $VCO_2$ trend line 176 showing the $VCO_2$ value over a time scale 174. The $VCO_2$ magnitude scale 172 is shown on the left hand side. The current $VCO_2$ value 181 is also shown. The lower portion of the exemplary display presents trend line 90 showing a target $EtCO_2$ over time (scale 74). The target $EtCO_2$ magnitude scale 88 is shown in the lower left corner. The current $EtCO_2$ target value setting 84 is also shown below the current $VCO_2$ value 181.

In one embodiment, the control system may alert a clinician if the $VCO_2$ value changes by more than a predetermined amount. The predetermined amount for the threshold $VCO_2$ change may be adjustable, for example by an operator 17 setting the threshold value through input device 15 (FIG. 1). For example, the system may provide an alert or an alarm if the $VCO_2$ value changes by more than 20% from a stable value. In another example, an alert may be provided in response to how quickly the $VCO_2$ value changes. For example, in malignant hyperthermia the $VCO_2$ value may increase very rapidly. In air embolism, the $VCO_2$ value may decrease very rapidly. In one embodiment, the $VCO_2$ value may change, e.g., 50% in a 30 second period of time and an alert is provided.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A method for automatically controlling ventilation of a patient, the method comprising:
receiving a target expiratory $CO_2$ concentration set by an operator as a control parameter for a ventilator to automatically maintain a constant expiratory $CO_2$ concentration of the patient;
measuring an actual expiratory $CO_2$ concentration;
comparing the actual expiratory $CO_2$ concentration to the target expiratory $CO_2$ concentration;
calculating an adjusted ventilation rate based on the comparison of the actual expiratory $CO_2$ concentration to the target expiratory $CO_2$ concentration in order to maintain the actual expiratory $CO_2$ concentration within a predetermined range of the target expiratory $CO_2$ concentration;
automatically ventilating the patient with the ventilator based on the adjusted ventilation rate so as to maintain the actual expiratory $CO_2$ concentration for the patient within the predetermined range of the target expiratory $CO_2$ concentration so as to maintain the constant expiratory $CO_2$ concentration of the patient; and
tracking the adjusted ventilation rate over time as an indicator of patient hemodynamic status.

2. The method of claim 1, further comprising displaying the target expiratory $CO_2$ concentration and the adjusted ventilation rate over time.

3. The method of claim 2, wherein the target expiratory $CO_2$ concentration and the adjusted ventilation rate over time are shown together with respect to a time axis.

4. The method of claim 1, further comprising displaying the target expiratory $CO_2$ concentration and a carbon dioxide clearance value over time as an indicator of patient hemodynamic status.

5. The method of claim 1, further comprising tracking the actual expiratory $CO_2$ concentration over time.

6. The method of claim 5, further comprising displaying the adjusted ventilation rate over time and the actual expiratory $CO_2$ concentration over time.

7. The method of claim 6, wherein the actual expiratory $CO_2$ concentration over time and the adjusted ventilation rate over time are shown together with respect to a time axis.

8. The method of claim 5, wherein the actual expiratory $CO_2$ concentration over time and carbon dioxide clearance value are shown together with respect to a time axis.

9. The method of claim 1, wherein the predetermined range is a predetermined percentage of the target expiratory $CO_2$ concentration.

10. The method of claim 9, wherein the predetermined percentage is less than or equal to 0.5%.

11. The method of claim 10, wherein the predetermined percentage is between 0.01% and 0.5%.

12. The method of claim 1, wherein the expiratory $CO_2$ concentration of the patient is maintained constant based on the target expiratory $CO_2$ concentration set by the operator until a new target expiratory $CO_2$ is set by the operator.

13. The method of claim 12, wherein, being held constant, the expiratory $CO_2$ concentration of the patient is not an indicator of patient hemodynamic status.

14. The method of claim 1, wherein tracking the adjusted ventilation rate over time as an indicator of patient hemodynamic status comprises generating an alert in response to a determination that a change in an alveolar minute volume value or a carbon dioxide clearance value exceeds a predetermined change value.

15. The method of claim 1, wherein tracking the adjusted ventilation rate over time as an indicator of patient hemodynamic status comprises generating an alert in response to a determination that a change in a carbon dioxide clearance value exceeds a predetermined rate of change value.

16. A method for automatically controlling ventilation of a patient, the method comprising:
receiving a target $EtCO_2$ for the patient set by an operator;
receiving an alveolar minute volume value for the patient;
measuring expiratory $CO_2$ in a gas expired from the patient;
calculating an actual $EtCO_2$;
comparing the actual $EtCO_2$ to the target $EtCO_2$; and
detecting that the actual $EtCO_2$ is not within a predetermined range of the target $EtCO_2$, and then:
adjusting the alveolar minute volume value based on the comparison;
automatically ventilating the patient based on the adjusted alveolar minute volume value; and
displaying a carbon dioxide clearance value over time to indicate the change in patient hemodynamic status.

17. The method of claim 16, further comprising tracking the alveolar minute volume value over time; and
displaying the target $EtCO_2$ and alveolar minute volume value over time together with respect to a time axis to indicate the change in patient hemodynamic status.

18. The method of claim 16, further comprising tracking the alveolar minute volume value over time; and
displaying the actual $EtCO_2$ and alveolar minute volume value over time together with respect to a time axis to indicate the change in patient hemodynamic status.

19. The method of claim 16, wherein the target $EtCO_2$ for the patient is received from a user input device operated by an operator.

20. The method of claim 16, wherein the predetermined range is a predetermined percentage of the target $EtCO_2$, wherein the predetermined percentage is between 0.01% and 0.5%.

21. A system for automatically ventilating a patient, the system comprising:
a ventilator;
a gas analyzer;
a controller;
a display;
wherein the controller is configured to:
receive a target $EtCO_2$ for the patient set by an operator;
receive an initial alveolar minute volume value for the patient;
receive from a gas analyzer an actual $EtCO_2$ in a gas expired from the patient;
compare the actual $EtCO_2$ to the target $EtCO_2$;
detect that the actual $EtCO_2$ is not within a predetermined range of the target $EtCO_2$, and then:
calculate an adjusted alveolar minute volume value;
automatically control the ventilator to ventilate the patient based on the adjusted alveolar minute volume value so as to maintain the actual $EtCO_2$ concentration for the patient within the predetermined range of the target $EtCO_2$ concentration so as to automatically maintain a constant expiratory $CO_2$ concentration of the patient; and
track an adjusted ventilation rate over time as an indicator of patient hemodynamic status.

22. The system of claim 21, wherein the controller is further configured to continually calculate the adjusted alveolar minute volume value as required to maintain the actual $EtCO_2$ is within the predetermined range of the target $EtCO_2$.

23. The system of claim 22, wherein the controller is further configured to operate the display to display the adjusted alveolar minute volume value with respect to time.

24. The system of claim 22, wherein the controller is further configured to operate the display to display the adjusted alveolar minute volume value and the target $EtCO_2$ with respect to time.

25. The system of claim 22, wherein the controller operates the display to display a carbon dioxide clearance value with respect to time.

26. The system of claim 21, wherein the controller is further configured to store the adjusted alveolar minute volume value to memory.

* * * * *